US011921073B2

(12) United States Patent
Gayrard et al.

(10) Patent No.: US 11,921,073 B2
(45) Date of Patent: Mar. 5, 2024

(54) FLUID SENSOR FOR SENSING PROPERTIES OF A FLUID COMPRISING A TUNING FORK MECHANICAL RESONATOR

(71) Applicant: Meas France, Toulouse (FR)

(72) Inventors: Fabien Gayrard, Toulouse (FR); Antoine Sirven, Toulouse (FR); Vincent Ducere, Toulouse (FR)

(73) Assignee: MEAS France, Toulouse (FR)

( * ) Notice: Subject to any disclaimer, the term of this patent is extended or adjusted under 35 U.S.C. 154(b) by 0 days.

(21) Appl. No.: 17/710,452

(22) Filed: Mar. 31, 2022

(65) Prior Publication Data

US 2022/0317077 A1 Oct. 6, 2022

(30) Foreign Application Priority Data

Mar. 31, 2021 (EP) .................................. 21305414

(51) Int. Cl.
 *G01N 27/06* (2006.01)
 *G01N 27/02* (2006.01)
 *G01N 27/07* (2006.01)
 *G01N 29/02* (2006.01)

(52) U.S. Cl.
 CPC ........... *G01N 27/07* (2013.01); *G01N 27/026* (2013.01); *G01N 29/022* (2013.01)

(58) Field of Classification Search
 CPC ..... G01N 27/026; G01N 27/07; G01N 29/022
 See application file for complete search history.

(56) References Cited

U.S. PATENT DOCUMENTS

| 4,245,200 | A | * | 1/1981 | Takahashi | ........... H03H 9/02559 333/194 |
| 6,177,756 | B1 | | 1/2001 | Yachi et al. | |
| 2006/0218996 | A1 | | 10/2006 | Matsiev et al. | |
| 2008/0174208 | A1 | * | 7/2008 | Takahashi | ................ H03H 9/21 310/361 |
| 2012/0285232 | A1 | * | 11/2012 | Swett | ...................... E21B 49/10 73/152.28 |
| 2013/0134981 | A1 | * | 5/2013 | Liu | ..................... G01N 29/2437 427/523 |

FOREIGN PATENT DOCUMENTS

| JP | S57124238 A | 8/1982 |
| JP | H11064004 A | 3/1999 |
| JP | 2000009469 A | 1/2000 |
| JP | 2000324332 A | 11/2000 |
| JP | 2001324332 A | 11/2001 |
| JP | 2011232263 A | 11/2011 |

(Continued)

OTHER PUBLICATIONS

Extended European Search Report, European Application No. 21305414. 1-1020, European Filing Date, Sep. 8, 2021.

(Continued)

*Primary Examiner* — Alesa Allgood
(74) *Attorney, Agent, or Firm* — Barley Snyder

(57) ABSTRACT

A fluid sensor includes a tuning fork mechanical resonator including a base and a tine projecting from the base along a longitudinal direction of the tine, and a pair of electrodes disposed on the tine. The base and the tine are formed from a piezoelectric material including lithium tantalate. The electrodes are exposed to a fluid.

11 Claims, 3 Drawing Sheets

(56) References Cited

FOREIGN PATENT DOCUMENTS

JP       2015505958 W    2/2015
WO       2013081806 A1   6/2012

OTHER PUBLICATIONS

Tomikawa et al., Analysis of electrical equivalent circuit elements of piezo-tuning forks by the finite element method, IEEE Transactions on Sonics and Ultrasonics, Jul. 1, 1978, pp. 206-212, vol. 25, No. 4, IEEE, US.

Office Action from the Japanese Patent Office dated Mar. 14, 2023 (with English translation thereof), corresponding to Application No. 2022-051554, 8 pages.

* cited by examiner

FLUID SENSOR FOR SENSING PROPERTIES OF A FLUID COMPRISING A TUNING FORK MECHANICAL RESONATOR

CROSS-REFERENCE TO RELATED APPLICATIONS

This application claims the benefit of the filing date under 35 U.S.C. § 119(a)-(d) of European Patent Application No. 21305414.1, filed on Mar. 31, 2021.

FIELD OF THE INVENTION

The present invention relates to a fluid sensor for sensing properties of a fluid.

BACKGROUND

Fluid sensors are known in the art and find their application in industrial machinery or transportation vehicles like construction equipment, agriculture vehicles, hydraulic systems, windmills or compressors. They are used to monitor one or more fluid parameters, like viscosity, density, dielectric constant or conductivity that are used to determine the quality of the fluid. The fluids can be oil, like non-electrically conductive oil, e.g. engine oil, transmission and axle oil, gear oil, power steering oil, hydraulic fluid or the like. Each application involves particular conditions like a temperature range, viscosity condition and mechanical requirements.

Such a fluid sensor is known from US 2006 218996 A1, which comprises a resonator with a quartz tuning fork and electrodes on the tines.

Such a resonator deforms upon application of a voltage and reciprocally electrically polarizes under the action of mechanical stress. Upon application of a voltage, the two tines oscillate and generate a response indicative of the physicochemical and electrical properties of the fluid wherein the fluid sensor is immersed. There is, however, a need for further improving the fluid sensors known in the art to enhance their lifetime and reliability in particular in extended temperature ranges and/or harsh environments.

SUMMARY

A fluid sensor includes a tuning fork mechanical resonator including a base and a tine projecting from the base along a longitudinal direction of the tine, and a pair of electrodes disposed on the tine. The base and the tine are formed from a piezoelectric material including lithium tantalate. The electrodes are exposed to a fluid.

BRIEF DESCRIPTION OF THE DRAWINGS

The invention will now be described by way of example with reference to the accompanying Figures, of which.

DETAILED DESCRIPTION OF THE EMBODIMENT(S)

Figure 1A:
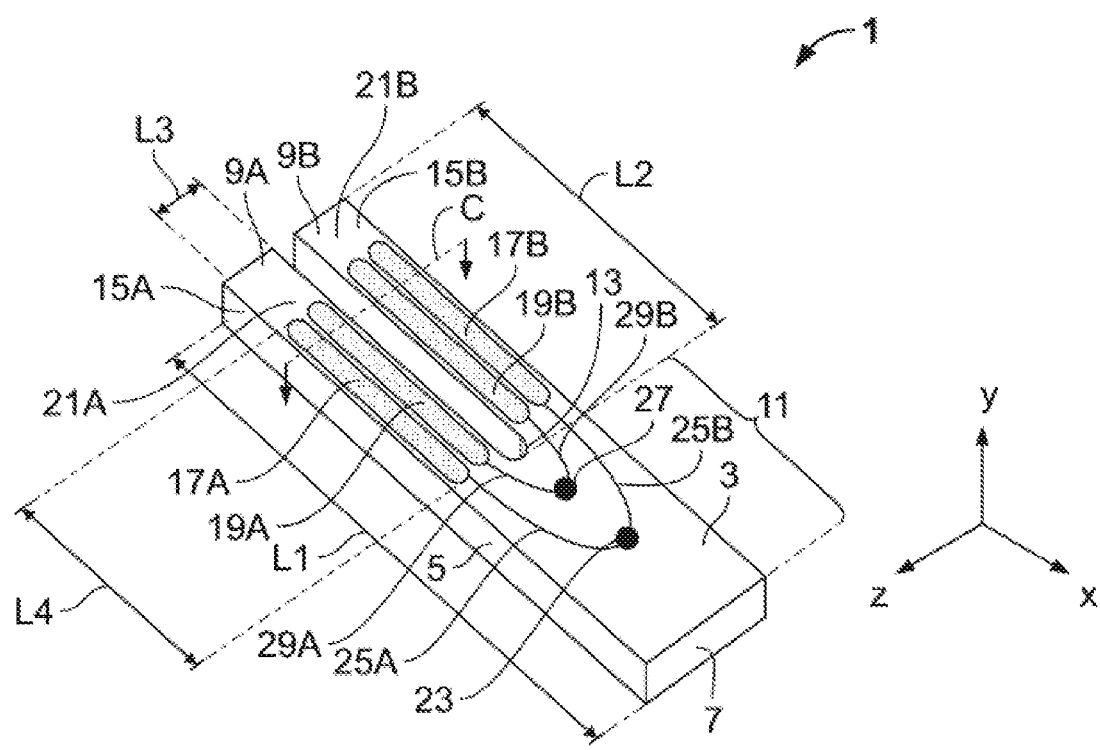
FIG. 1a is a perspective view of a fluid sensor according to a first embodiment.

The accompanying drawings are incorporated into the specification and form a part of the specification to illustrate several embodiments of the present invention. These drawings, together with the description, explain the principles of the invention. The drawings are merely for the purpose of illustrating examples of how the invention can be made and used, and are not to be construed as limiting the invention to only the illustrated and described embodiments.

Furthermore, several aspects of the embodiments may form—individually or in different combinations—solutions according to the present invention. The following described embodiments thus can be considered either alone or in an arbitrary combination thereof. Further features and advantages will become apparent from the following more particular description of the various embodiments of the invention, as illustrated in the accompanying drawings, in which like references refer to like elements.

The present invention will now be described with reference to the attached Figures. Various structures, systems and devices are schematically depicted in the drawings for purposes of explanation only and so as to not obscure the present disclosure with details, which are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary or customary meaning as understood by those skilled in the art, is intended to be implied by consistent usage of the term or phrase herein.

FIG. 1a illustrates a fluid sensor 1 comprising a tuning fork mechanical resonator 3 according to a first embodiment of the invention. The fluid sensor 1 can be mounted to a support, so as to be maintained in a fluid according to known assembly methods. In use, the fluid sensor 1 is at least partially immersed in a fluid for sensing its properties. The fluid can be an oil for industrial machines or for transportation vehicles.

The tuning fork mechanical resonator 3 comprises a body 5 having a length L1 between one first free-end 7 and opposite second free-ends 9A, 9B along the X-axis of the Cartesian coordinates illustrated in FIG. 1a. The body 5 has a base 11, extending along the X-axis of the Cartesian coordinates, from the free-end 7 to a junction region 13 of the body 5.

From the junction region 13, in the illustrated embodiment of FIG. 1a, two tines 15A, 15B extend distinctly from each other to their corresponding free-ends 9A, 9B along a longitudinal direction of the tines 15A, 15B. In another embodiment, only one single tine can extend from the junction region 13 of the body 5 of the tuning fork mechanical resonator 3. In a further embodiment, three tines or more can extend from the junction region 13 of the body 5 of the tuning fork mechanical resonator 3. The base 11 and the tines 15A, 15B are formed from a piezoelectric material.

In the embodiment shown in FIG. 1a, the two tines 15A, 15B project from the base 11 along the X-axis of the Cartesian coordinate. The longitudinal direction of the tines 15A, 15B is thus parallel to the X-axis of the Cartesian coordinate shown in FIG. 1a. In the illustrated embodiment of FIG. 1a, the tines 15A, 15B have a rectangular cross-section. In a variant, a cross-section of the tines 15A, 15B corresponds to the cross-section of a parallelepiped. In the first embodiment, the tines 15A, 15B are symmetrical to each other with respect to the X-axis of the Cartesian coordinates. In a variant, the tines 15A, 15B can be asymmetrical.

The reference number followed by the letter "A" refers to the left tine illustrated in FIG. 1a, while the letter "B" refers to the right tine illustrated in FIG. 1a.

Figure 2:
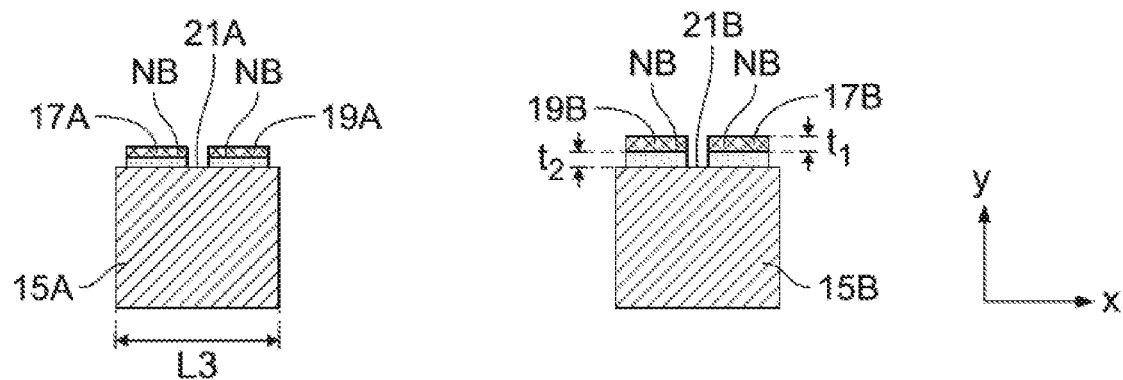
FIG. 2 is a sectional view of the fluid sensor of the first embodiment, taken along line C in FIG. 1.

The length L2 shown in FIG. 2 represents the length between the junction region 13 and the free-ends 9A, 9B, i.e. L2 indicates the length of the tines 15A, 15B. Each tine 15A, 15B has a width L3. The dimensions L1 to L3 are further described hereafter in reference to Table 1.

Each tine 15A, 15B is provided with electrodes 17A-B, 19A-B, as shown in FIG. 1a. The electrodes 17A-B, 19A-B have an oblong shape of length L4 along the longitudinal direction of the two tines 15A, 15B from the base 11, i.e. along the X-axis of the Cartesian coordinate.

In a variant, the electrodes 17A-B, 19A-B can have a rectangular shape.

In the first embodiment illustrated in FIG. 1a, two electrodes 17A-B (respectively 19A-B) are provided on or over a surface 21A (respectively a surface 21B) of the tine 15A (respectively the tine 15B). In a variant, the electrodes 17A, 17B, 19A, 19B can be at least partially embedded in the tines 15A, 15B. In an embodiment of a tuning fork mechanical resonator comprising one single tine, the single tine can be provided with two electrodes on or over a surface of the single tine, or, at least partially embedded in the single tine. Such electrode arrangement allows generating larger electric fields outside the piezoelectric material. Hence, the influence of the piezoelectric material on the measures of the fluid parameters can be reduced while measuring the properties of the fluid. Furthermore, this arrangement allows determining the electrical resistivity of the fluid.

Figure 1B:
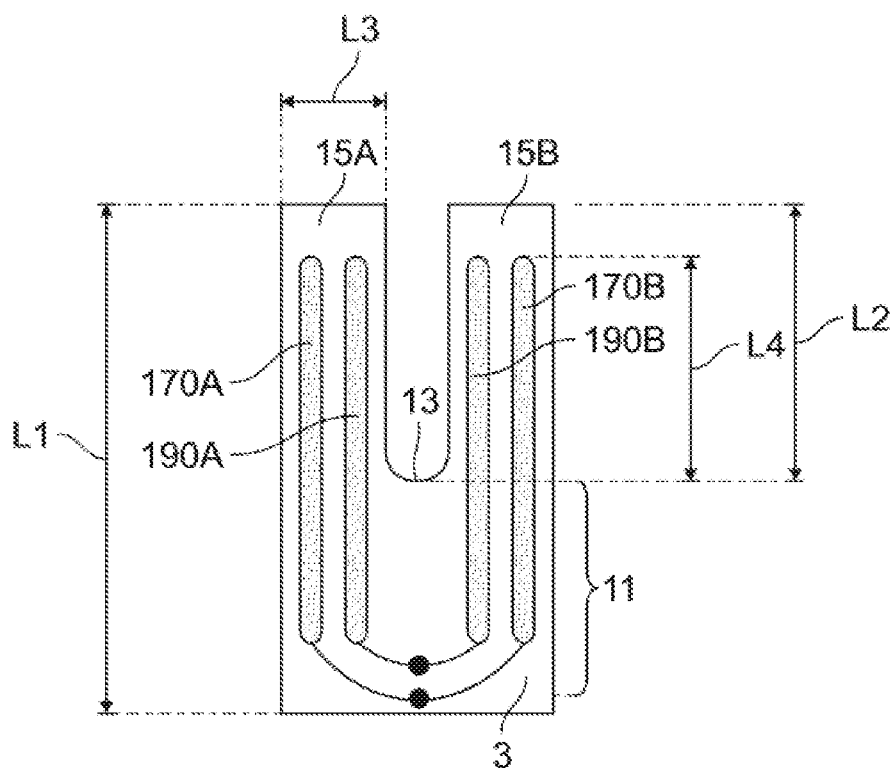
FIG. 1b is a perspective view of a fluid sensor according to a second embodiment.

In a second embodiment, as illustrated in FIG. 1b, the electrodes 170A-B, 190A-B extend along the longitudinal direction of the tines 15A, 15B so as to be further provided on or over the base 11 of the tuning fork mechanical resonator 3. In the second embodiment of FIG. 1b, the length L4 corresponds to the length of the portion of each electrodes 170A-B, 190A-B provided on or over the tines 15A, 15B. In other words, in the second embodiment, the length L4 does not correspond to the total length of each electrodes 170A-B, 190A-B.

Hence, in both embodiments shown in FIGS. 1a and 1b, the length L4 represents the length of a portion of the electrodes 17A-B, 170A-B, 19A-B, 190A-B on or over the tines 15A, 15B, i.e. the length of a portion of the electrodes 17A-B, 170A-B, 19A-B, 190A-B comprises between the junction region 13 and the free-ends 9A, 9B of the tines 15A, 15B.

In the first embodiment of FIG. 1a, the length L4 further corresponds to the total length of the electrodes 17A-B, 19A-B, while in the second embodiment of FIG. 1b, the length L4 only corresponds to a portion of the electrodes 170A-B, 190A-B.

As shown in the cross-sectional view of the fluid sensor 1 according to the cutting plan represented in FIG. 2, the electrodes 17A, 19A (respectively the electrodes 17B, 17B) are formed by a noble layer NB provided on or over the surface 21A (respectively the surface 21B) of the tine 15A (respectively the tine 15B). In an embodiment, the noble layer NB is a layer of gold. The noble layer NB has a thickness t1 between 10 nm and 600 nm. In an embodiment, the noble layer NB has a thickness of 200 nm.

As represented in FIG. 2, a thin adhesion layer of chromium or titanium of thickness t2 can be provided underneath the noble layer NB, and, on or above the surfaces 21A, 21B. Such adhesion layer can have a thickness between 5 and 40 nm. An adhesion layer improves the adhesion of the noble layer NB on the piezoelectric material of the tines 15A, 15B. Thereby, it improves the robustness of the layer stack of the fluid sensor 1. Hence, a delamination or damage due to chemical or mechanical stress (like thermal shocks, vibrations, mechanical shock . . . ) can be reduced.

As shown in FIG. 1a, the electrodes 17A, 17B are in electrical connection with a common first contact pad 23 through respective conductive paths (e.g. leads) 25A, 25B and are therefore in common electrical communication with each other. Similarly, the electrodes 19A, 19B are in electrical connection with a common first contact pad 27 through respective conductive paths (e.g. leads) 29A, 29B and are therefore in common electrical connection with each other. The electrode 17A, located on the tine 15A, is electrically connected to the electrode 17B located on the tine 15B and to the contact pad 23. Similarly, the electrode 19A, located on the tine 15A, is electrically connected to the electrode 19B located on the tine 15B and to the contact pad 27. The contact pads 23, 27 are used to electrically connect the electrodes 17A-B, 19A-B to a control unit of the fluid sensor 1.

Figure 3:
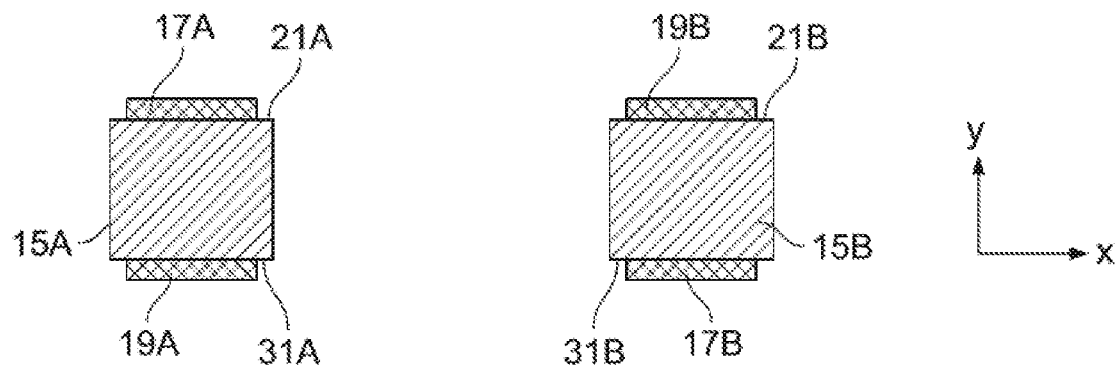
FIG. 3 is a sectional view of a fluid sensor according to a third embodiment.
Figure 4:
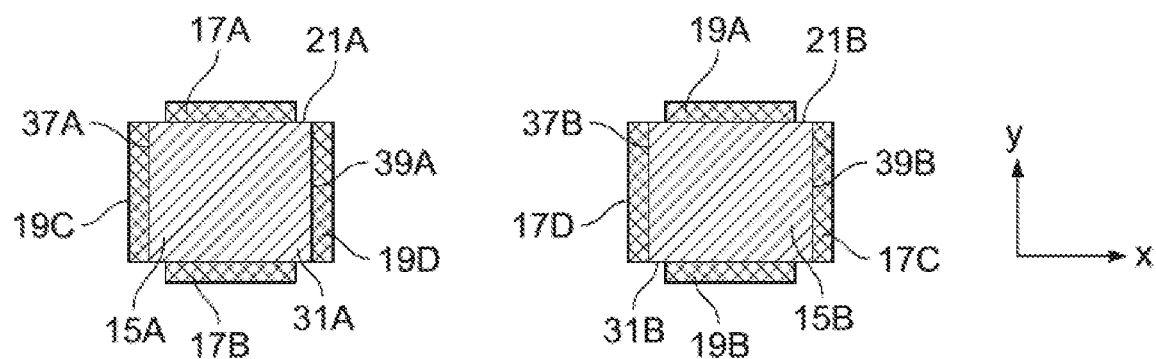
FIG. 4 is a sectional view of a fluid sensor according to a fourth embodiment.

FIGS. 3 and 4 illustrate two embodiments of electrodes arrangement according to the present invention.

In a third embodiment shown in FIG. 3, each tine 15A, 15B comprises two electrodes 17A-B, 19A-B. An electrode 17A is provided on or over the surface 21A of the tine 15A. An electrode 17B is provided on or over the surface 31B of the tine 15B. An electrode 19A is provided on or over a surface 31A of the tine 15A. An electrode 19B is provided on or over the surface 21B of the tine 15B. The surfaces 31A, 31B are opposite to the surfaces 21A, 21B along the Y-axis of the Cartesian coordinate. In an embodiment of a tuning fork mechanical resonator comprising one single tine, the single tine could also be provided with two electrodes on or over opposite surfaces of the single tine. The same applies in an embodiment of a tuning fork mechanical resonator comprising three or more tines.

In a fourth embodiment shown in FIG. 4, each tine 15A, 15B comprises four electrodes 17A-D, 19A-D. The electrodes 17A-B and 17C-D can be connected or not. The electrodes 19A-B and 19C-D can be connected or not. Each electrode 17A-B, 19A-B, 17C-D, 19C-D is provided on or over a different face 21A-31A, 21B-31B, 39B-37B, 37A-39A of each tine 15A, 15B. For each tine 15A, 15B, the surface 37A-B is opposite to the surface 39A-B along the Y-axis of the Cartesian coordinate. In an embodiment of a tuning fork mechanical resonator comprising one single tine, the single tine could also be provided with four electrodes on or over a surface of the single tine. The same applies in an embodiment of a tuning fork mechanical resonator comprising three or more tines.

In any embodiments of the present invention, the electrodes 17A, 17B, 19A, 19B are configured to be exposed to the fluid in which the sensor 1 is immersed. Hence, the electrodes 17A, 17B, 19A, 19B have a direct surface contact with the fluid in which the fluid sensor 1 is immersed.

Under application of a voltage by the electrodes 17A, 17B, 19A, 19B (17C-17D, 19C-19D), the free-end 9A, 9B of each tines 15A, 15B is capable of displacement in a fluid relative to the base 11 of the tuning fork mechanical resonator 3. The pair of tines 15A, 15B can thus also be referred to as vibrating arms of the tuning fork mechanical resonator 3. The oscillation of the tines 15A, 15B allows generating a response indicative of the physicochemical and electrical properties of the fluid wherein the fluid sensor 1 is immersed.

In use, the electrodes 17A, 17B, 19A, 19B (17C-17D, 19C-19D) are exposed to the fluid, and electric fields can be generated within and outside the piezoelectric material of the tuning fork mechanical resonator 3. As the electric fields are generated in the fluid, the fluid sensor 1 is able to measure the electrical resistivity of the fluid, in addition of the viscosity, the density and the dielectric constant.

The electrode (17A-B, 19A-B, 17C-17D, 19C-19D) arrangement shown in FIG. 4 allows generating an even larger electric field outside the piezoelectric material of the tuning fork mechanical resonator 3 than in the embodiments of FIGS. 1a, 1b, 2 and 3, which renders the fluid sensor 1 even more adapted for measuring the electrical resistivity of the fluid.

According to the present invention, the body 5 of the tuning fork mechanical resonator 3 comprises lithium tantalate (LiTaO3) as piezoelectric material. Lithium tantalate exhibits a piezoelectric effect, and can thus be used for a tuning fork mechanical resonator. Because of its advantageous mechanical properties, the use of lithium tantalate renders the fluid sensor 1 more robust compared to tuning fork mechanical resonator made of lithium niobate or quartz. Hence, the reliability of the fluid sensor 1 is improved. The lithium tantalate furthermore is chemically stable. Thus, the lifetime of such fluid sensor 1 can advantageously be increased with respect to the tuning fork devices known from the state of the art.

Figure 5:
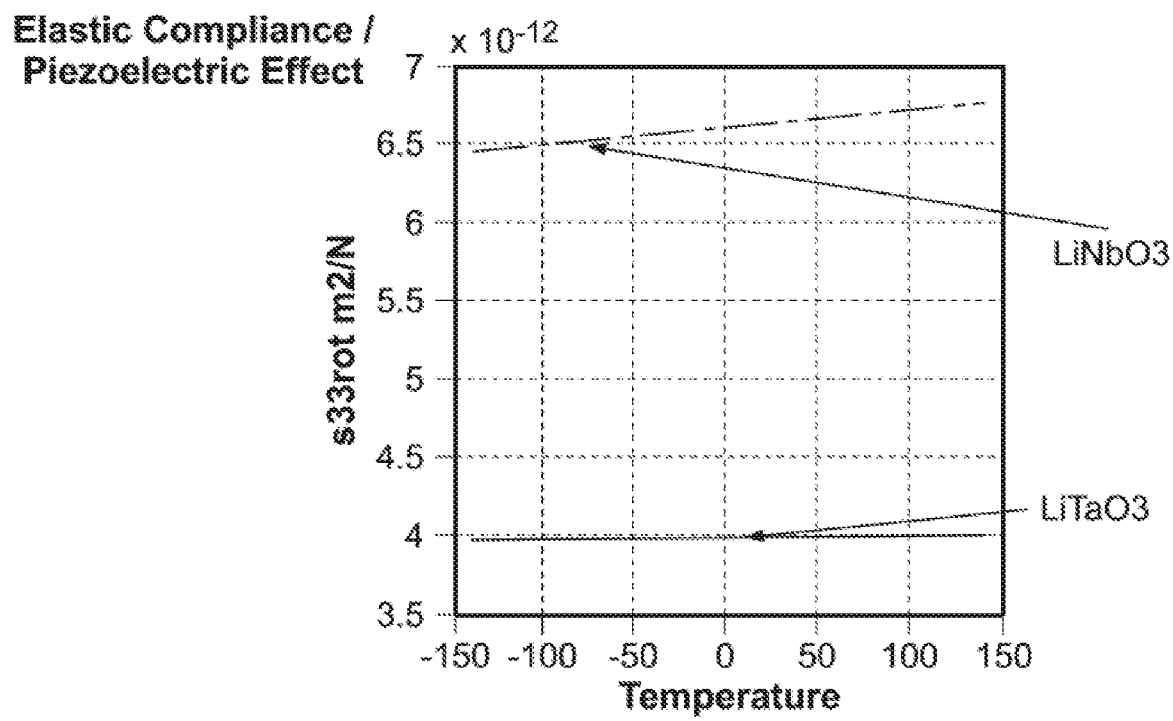
FIG. 5 is a graph of the elastic compliance/piezoelectric effect of the lithium tantalate and lithium niobiate in function of the temperature at a crystal cut angle of the lithium tantalate comprised between 110 and 140 degrees on rotated Y-cut with respect to the X-axis.

In an embodiment, the surface 21A of the piezoelectric material on or over which the electrodes 17A-B, 19A-B are provided has a crystal cut angle comprised between 110 and 140 degrees on rotated Y-cut about the X-axis, the tine strain being along the X-axis. In this crystal cut range (i.e. a crystal cut angle comprised between 110 and 140 degrees on rotated Y-cut about the X-axis), as illustrated by the curve of FIG. 5, the piezoelectric effect provided by the lithium tantalate (LiTaO3) is less temperature dependent compared to lithium niobiate (LiNbO3). Hence, the fluid sensor 1 can be used in broad ranges of temperature and viscosity conditions.

As a result, the fluid sensor 1 comprising lithium tantalate as piezoelectric material has an improved lifetime and reliability in particular in extended temperature ranges and/or harsh environments than the known fluid sensors with a resonator made of quartz.

In an embodiment, the body 5 can comprises different materials, thus a combination of lithium tantalate and one or more of quartz, zirconate titanate (PZT), lithium niobiate, berlinite or zinc oxide, according to the desired application. For example, a tine can be made from multilayers of different materials comprising a non-piezoelectric material like silicon nitride, silicon carbide or silicon oxide, according to the desired application.

In order to further enhance the lifetime and the reliability in harsh environments, in particular in high viscosity conditions, for example in a viscosity range above 50 cP and up to 20,000 cP, the fluid sensor 1 has the following dimensions (see Table 1 below). The dimensions L1 to L4 in Table 1 corresponds to the dimensions previously described with respect to FIGS. 1a and 1b.

TABLE 1

| L1 | length of the body 5 of the resonator 3 | 6-30 mm (or 10-13 mm) |
|----|------------------------------------------|------------------------|
| L2 | length of the tines 15A, 15B | 3-10 mm |
| L3 | width of the tines 15A, 15B | 0.5-2 mm |
| L4 | lengths of the electrodes 17A-B, 19A-B (or portion of the electrodes) on or over the tines 15A, 15B | 3-10 mm |

Figure 6:
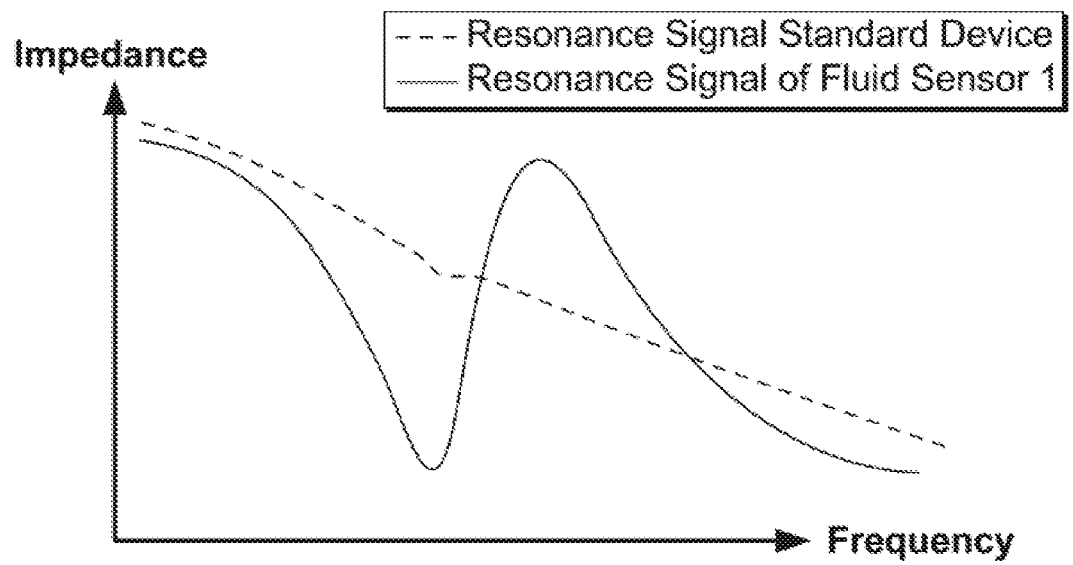
FIG. 6 is a graph of the impedance in function of the frequency in a viscosity range between 50 cP and 2.000 cP, for a standard tuning-fork-type device and for a fluid sensor according to the present invention.

The larger dimensions L1-L4 of the fluid sensor 1 comprising lithium tantalate provide, in addition to realizing a more robust fluid sensor 1 than known tuning forks of smaller size, a fluid sensor 1 exhibiting a resonance signal of better quality in high viscosity fluid condition. FIG. 6 represents the impedance in function of the frequency in a viscosity range between 50 cP and 2,000 cP, for a standard tuning-fork-type device (having L1=6 mm, L2=4 mm and L3=0.5 mm) and for a fluid sensor 1 according to the present invention having dimensions as disclosed in Table 1. Hence, as shown in FIG. 6, the size of the fluid sensor 1 is indeed large enough for avoiding that the resonance signal is damped, in particular in high viscosity fluid condition, i.e. between 50 cP and up to 20,000 cP, countering the high shear forces of viscous fluid. The above-defined dimensions L1-L4 also apply to the embodiments of a fluid sensor provided with one single tine or with three or more tines.

Although the embodiments have been described in relation to particular examples, the invention is not limited and numerous alterations to the disclosed embodiments can be made without departing from the scope of this invention. The various embodiments and examples are thus not intended to be limited to the particular forms disclosed. Rather, they include modifications and alternatives falling within the scope of the claims and individual features can be freely combined with each other to obtain further embodiments or examples according to the invention.

What is claimed is:

1. A fluid sensor, comprising:
   a tuning fork mechanical resonator including a base and a tine projecting from the base along a longitudinal direction of the tine, the base and the tine are formed from a piezoelectric material including lithium tantalate; and
   a pair of electrodes disposed on or over a surface of the tine, each of the electrodes is disposed on or over a different face of the tine, the electrodes have a direct surface contact with a fluid in which the fluid sensor is immersed.

2. The fluid sensor of claim 1, wherein the tine is one of a pair of tines of the tuning fork mechanical resonator projecting from the base along the longitudinal direction.

3. The fluid sensor of claim 1, wherein at least one of the electrodes is provided on a surface of the lithium tantalate having a crystal cut angle between 110 and 140 degrees on a rotated Y-cut about an X-axis.

4. The fluid sensor of claim 1, wherein the tine has a rectangular cross-section.

5. The fluid sensor of claim 1, wherein the pair of electrodes are part of four electrodes of the fluid sensor.

6. The fluid sensor of claim 1, wherein each electrode is disposed on or over the base of the tuning fork mechanical resonator.

7. The fluid sensor of claim 1, wherein each electrode has an oblong shape.

8. The fluid sensor of claim 1, wherein a portion of each electrode provided on or over a face of the tine has a length along the longitudinal direction between 3 mm and 10 mm.

9. The fluid sensor of claim 8, wherein the tine has a width along a direction transverse to the longitudinal direction between 0.5 mm and 2 mm.

10. The fluid sensor of claim 1, wherein a length of the tuning fork mechanical resonator from the base to a free end of the tine is between 6 mm and 30 mm.

11. The fluid sensor of claim 10, wherein the length of the tuning fork mechanical resonator from the base to the free end is between 10 mm and 13 mm.

* * * * *